US007167755B2

(12) United States Patent
Seeberger et al.

(10) Patent No.: US 7,167,755 B2
(45) Date of Patent: Jan. 23, 2007

(54) ADAPTIVE SOFTWARE CONFIGURATION FOR A MEDICAL DEVICE

(75) Inventors: Michael Seeberger, Bayport, MN (US); Scott Vanderlinde, Plymouth, MN (US); James Kalgren, Lino Lakes, MN (US); Par Lindh, Maple Grove, MN (US); Kristine M. Larsen-Kelly, Lino Lakes, MN (US); Mitchell Lanz, Maple Grove, MN (US); Jeffrey M. Thompson, Minneapolis, MN (US); John A. Dyjach, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 109 days.

(21) Appl. No.: 10/958,628

(22) Filed: Oct. 5, 2004

(65) Prior Publication Data

US 2006/0074463 A1    Apr. 6, 2006

(51) Int. Cl.
*A61N 1/08* (2006.01)
(52) U.S. Cl. .................................................. 607/59
(58) Field of Classification Search ................ 607/30, 607/32, 59
See application file for complete search history.

(56) References Cited

U.S. PATENT DOCUMENTS

| 4,236,524 A | 12/1980 | Powell et al. |
| 4,273,133 A | 6/1981 | Hartlaub et al. |
| 4,407,288 A | 10/1983 | Langer et al. |
| 4,809,697 A | 3/1989 | Causey, III et al. |
| 4,940,052 A | 7/1990 | Mann et al. |
| 5,076,272 A | 12/1991 | Ferek-Petric |
| 5,080,096 A | 1/1992 | Hooper et al. |
| 5,113,869 A | 5/1992 | Nappholz et al. |
| 5,127,404 A | 7/1992 | Wyborny et al. |
| 5,217,010 A | 6/1993 | Tsitilk et al. |
| 5,312,446 A | 5/1994 | Holschbach et al. |
| 5,342,408 A | 8/1994 | deCoriolis et al. |
| 5,360,437 A | 11/1994 | Thompson |
| 5,387,229 A | 2/1995 | Poore |
| 5,456,691 A | 10/1995 | Snell |
| 5,456,692 A | 10/1995 | Smith, Jr. et al. |

(Continued)

FOREIGN PATENT DOCUMENTS

WO    WO-9110471 A1    7/1991

(Continued)

OTHER PUBLICATIONS

"International Search Report and Written Opinion for Application No. PCT/US2005/035651, date mailed Feb. 20, 2006", 14 Pages.

*Primary Examiner*—Robert Pezzuto
*Assistant Examiner*—Yun Haeng Lee
(74) *Attorney, Agent, or Firm*—Schwegman, Lundberg, Woessner, & Kluth, P.A.

(57) ABSTRACT

This document describes, among other things, a method of operating a medical device comprising updating a regulatory approval status stored in at least one of the medical device or a second device operable to communicate with the medical device, and enabling or disabling the at least one function in the medical device based on the regulatory approval status. The regulatory approval status corresponds to at least one function performable by the medical device.

40 Claims, 6 Drawing Sheets

U.S. PATENT DOCUMENTS

| | | | |
|---|---|---|---|
| 5,565,005 A | 10/1996 | Erickson et al. | |
| 5,607,458 A | 3/1997 | Causey, III et al. | |
| 5,626,623 A | 5/1997 | Kieval et al. | |
| 5,653,735 A | 8/1997 | Chen et al. | |
| 5,653,737 A | 8/1997 | van Lake | |
| 5,693,076 A | 12/1997 | Kaemmerer | |
| 5,722,998 A | 3/1998 | Prutchi et al. | |
| 5,725,559 A | 3/1998 | Alt et al. | |
| 5,735,887 A | 4/1998 | Barreras, Sr. et al. | |
| 5,785,660 A | 7/1998 | van Lake et al. | |
| 5,792,201 A | 8/1998 | Causey, III et al. | |
| 5,792,204 A | 8/1998 | Snell | |
| 5,800,473 A | 9/1998 | Faisandier | |
| 5,836,989 A | 11/1998 | Shelton | |
| 5,843,138 A | 12/1998 | Evers et al. | |
| 5,891,182 A | 4/1999 | Fleming | |
| 5,899,931 A | 5/1999 | Deschamp et al. | |
| 5,902,325 A | 5/1999 | Condie et al. | |
| 5,941,906 A | 8/1999 | Barreras, Sr. et al. | |
| 6,073,049 A | 6/2000 | Alt et al. | |
| 6,088,618 A | 7/2000 | Kerver | |
| 6,157,859 A | 12/2000 | Alt | |
| 6,200,265 B1 | 3/2001 | Walsh et al. | |
| 6,243,608 B1 | 6/2001 | Pauly et al. | |
| 6,308,099 B1 | 10/2001 | Fox et al. | |
| 6,321,117 B1 | 11/2001 | Koshiol et al. | |
| 6,363,282 B1 * | 3/2002 | Nichols et al. | 607/30 |
| 6,427,088 B1 | 7/2002 | Bowman, IV et al. | |
| 6,512,954 B1 | 1/2003 | Fox et al. | |
| 6,535,766 B1 | 3/2003 | Thompson et al. | |
| 6,562,001 B1 | 5/2003 | Lebel et al. | |
| 6,564,105 B1 | 5/2003 | Starkweather et al. | |
| 6,571,128 B1 | 5/2003 | Lebel et al. | |
| 6,577,899 B1 | 6/2003 | Lebel et al. | |
| 6,584,356 B1 | 6/2003 | Wassmund et al. | |
| 6,585,644 B1 | 7/2003 | Lebel et al. | |
| 6,618,618 B1 | 9/2003 | Kalgren et al. | |
| 6,622,045 B1 | 9/2003 | Snell et al. | |
| 6,625,488 B1 | 9/2003 | Poore et al. | |
| 6,635,014 B1 | 10/2003 | Starkweather et al. | |
| 6,648,821 B1 | 11/2003 | Lebel et al. | |
| 6,659,948 B1 | 12/2003 | Lebel et al. | |
| 6,665,565 B1 | 12/2003 | Stomberg et al. | |
| 6,668,196 B1 | 12/2003 | Villegas et al. | |
| 6,681,003 B1 | 1/2004 | Linder et al. | |
| 6,687,546 B1 | 2/2004 | Lebel et al. | |
| 6,694,191 B1 | 2/2004 | Starkweather et al. | |
| 6,733,446 B1 | 5/2004 | Lebel et al. | |
| 6,738,670 B1 | 5/2004 | Almendinger et al. | |
| 6,738,671 B1 | 5/2004 | Christophersom et al. | |
| 6,740,075 B1 | 5/2004 | Lebel et al. | |
| 6,758,810 B1 | 7/2004 | Lebel et al. | |
| 6,792,311 B1 | 9/2004 | Fox et al. | |
| 6,847,843 B1 | 1/2005 | Mouchawar et al. | |
| 6,868,288 B1 | 3/2005 | Thompson | |
| 6,882,883 B1 | 4/2005 | Condie et al. | |
| 2002/0032470 A1 | 3/2002 | Linberg | |
| 2002/0077668 A1 | 6/2002 | Kalgren et al. | |
| 2002/0082665 A1 | 6/2002 | Haller et al. | |
| 2002/0143372 A1 | 10/2002 | Snell et al. | |
| 2002/0177878 A1 | 11/2002 | Poore et al. | |
| 2003/0028219 A1 | 2/2003 | Powers et al. | |
| 2003/0088292 A1 | 5/2003 | Anderson et al. | |
| 2003/0114897 A1 | 6/2003 | Von Arx et al. | |
| 2003/0139778 A1 | 7/2003 | Fischell et al. | |
| 2003/0170901 A1 | 9/2003 | Kippenhan et al. | |
| 2003/0204147 A1 | 10/2003 | Condie et al. | |
| 2003/0220673 A1 | 11/2003 | Snell | |
| 2004/0064165 A1 | 4/2004 | Thompson | |
| 2004/0068199 A1 | 4/2004 | Echauz et al. | |
| 2004/0138724 A1 | 7/2004 | Sieracki et al. | |
| 2004/0143304 A1 | 7/2004 | Hall et al. | |
| 2004/0143305 A1 | 7/2004 | Kalgren et al. | |
| 2004/0210255 A1 | 10/2004 | Degroot et al. | |
| 2004/0267233 A1 | 12/2004 | Ginggen | |
| 2005/0049656 A1 | 3/2005 | Petersen et al. | |
| 2005/0107839 A1 | 5/2005 | Sanders | |

FOREIGN PATENT DOCUMENTS

| | | |
|---|---|---|
| WO | WO-9200779 A1 | 1/1992 |
| WO | WO-9203182 A1 | 3/1992 |
| WO | WO-9640366 A1 | 12/1996 |
| WO | WO-01475999 A1 | 7/2001 |
| WO | WO-04041359 A1 | 5/2004 |
| WO | WO-05021092 A1 | 3/2005 |

* cited by examiner

ADAPTIVE SOFTWARE CONFIGURATION FOR A MEDICAL DEVICE

TECHNICAL FIELD

The field generally relates to medical devices and, in particular, but not by way of limitation, to systems and methods for managing functions performed by medical devices.

BACKGROUND

Patient care often includes use of advanced medical devices. These devices typically automatically perform a host of functions including therapeutic functions, for example, to deliver therapy to a patient or patients, or to perform diagnostic functions such as automatically running tests on patients. These functions are also sometimes referred to as features of the medical devices. Examples of medical devices include, blood glucose meters, insulin pumps, urinalysis devices, fetal heart monitoring devices, blood test meters, sleep apnea or hypopnea detection devices, and sleep apnea therapy devices like continuous positive airway pressure (CPAP) devices, blood pressure cuffs and weight scales. Implantable medical devices (IMDs) are devices designed to be implanted into a patient. Some examples of IMDs include cardiac rhythm management (CRM) devices such as implantable pacemakers and implantable cardioverter defibrillators (ICDs). The devices are used to treat patients using electrical therapy and to aid a physician or caregiver in patient diagnosis through internal monitoring of a patient's condition. IMDs may also include electrical leads that are either separate from, or connected to, a CRM device. Electrical leads connected to CRM devices are typically located in or near a heart to provide electrical therapy to the heart. The electrical leads are also in communication with sense amplifiers of the CRM devices to monitor intrinsic electrical heart activity of a patient. Other examples of IMDs include implantable insulin pumps or devices implanted to administer drugs to a patient. Additionally, some medical devices are able to communicate with other devices by wireless communication signals.

Often, the full functionality of the medical devices is not available or useful to a patient or caregiver. The functions actually needed or used may be a subset of the available functions, such as to match the device to specific patient needs. If the medical device is implantable, a device parameter, device configuration, or patient parameter may change. This, in turn, may require changing the functions available in the medical device.

Additionally, when new functions are developed, the functions may need to be approved by one or more governmental, quasi-governmental, or other regulatory bodies, such as the Food and Drug Administration (FDA) of the United States Government. Gaining regulatory approval is often a long process. For example, it may involve lengthy clinical trials. If an IMD is marketed worldwide, an IMD manufacturer needs to gain approval for the new functions from several regulatory bodies in different geographical areas of the world.

SUMMARY

The present inventors have recognized a need for improved management of functions of medical devices. This document discusses, among other things, systems and methods provided for managing functions of medical devices. A method example includes a method of configuring a medical device. The method comprises updating a regulatory approval status stored in at least one of the medical device or a second device operable to communicate with the medical device, and enabling or disabling the at least one function in the medical device based on the regulatory approval status. The regulatory approval status corresponds to at least one function performable by the medical device.

A system example comprises an implantable medical device (IMD) and a second device. The IMD includes a communication circuit, a memory circuit and a controller circuit coupled to the at least one memory circuit and communication circuit. The memory circuit of the IMD stores instruction code executable by the controller circuit to perform at least one function and to enable or disable the at least one function. The second device includes a communication circuit, a memory circuit and a controller circuit coupled to the at least one memory circuit and the communication circuit. The controller circuit of the second device executes instructions to communicate with the IMD. At least one of the memory circuits of the IMD and the second device stores a status identifier corresponding to a regulatory approval status of the at least one function. The status identifier is used to enable or disable the at least one function.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
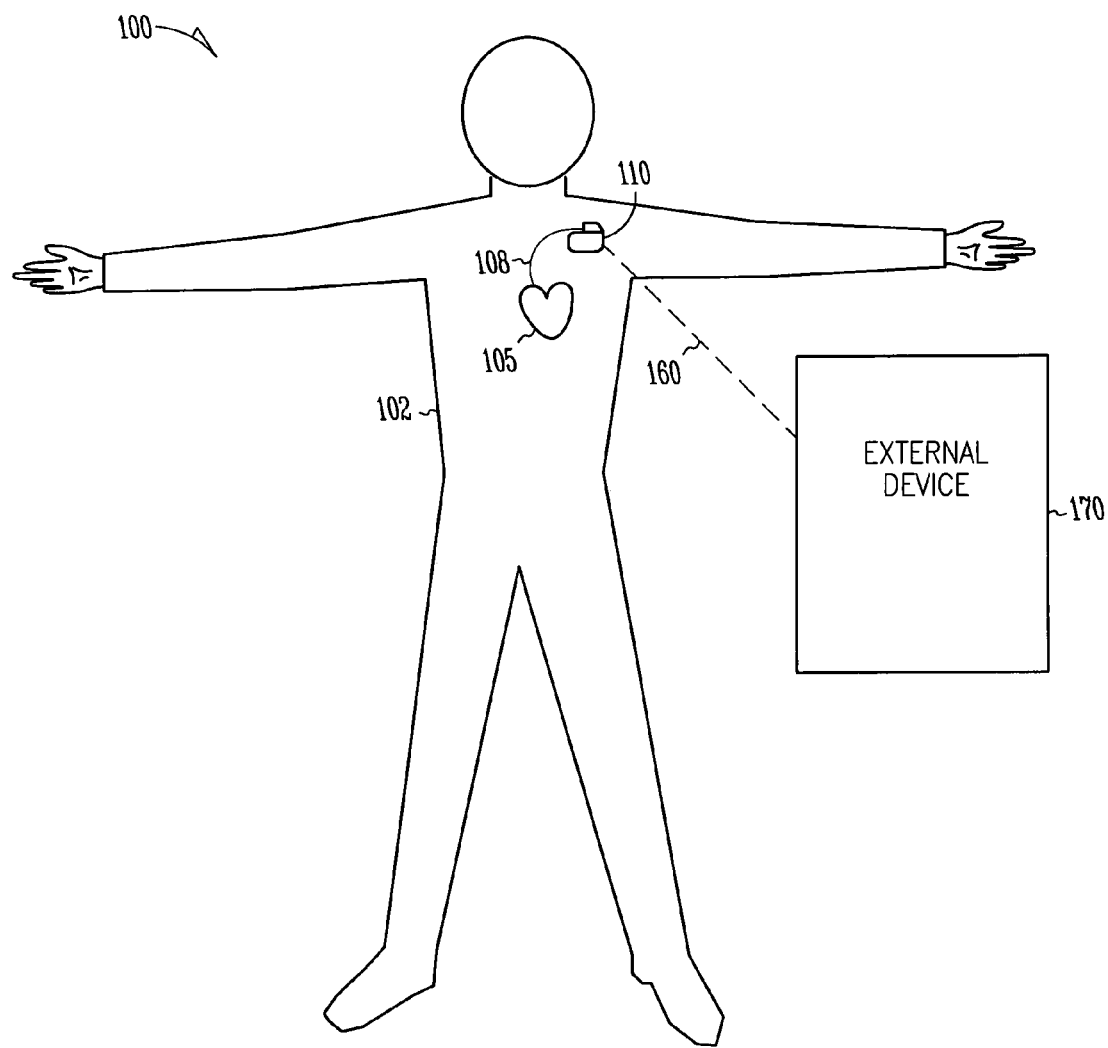
FIG. 1 is an illustration of an embodiment of a system that uses an implantable medical device.

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention. In this document, the term "or" is used to refer to a nonexclusive or, unless otherwise indicated.

The present application discusses, among other things, systems and methods for managing functions performed by medical devices. Medical devices are often complex and are typically capable of providing many different functions. A patient may not require all of the functionality of a particular device. However, the functionality required from the device may change, such as when information related to the patient or the device is obtained. This information includes information related to a patient, such as a condition of the patient or change in condition of the patient. A change in the patient condition may result in a need for a different device having different functionality. If the device is an implantable device, the need for a different device typically results in another implant procedure, which typically involves both increased cost and risk.

This information related to the patient or the device may also include information related to changes in device-measured parameters. Such parameters may be measured after prompting by a user or done automatically by the device. Typically, the information is communicated to a user by the medical device itself or by a second device used to communicate with the medical device. The information is typically given to a user through a user interface. The user may then change the functionality of the device using the user interface. There may be adverse delays in enabling or disabling the proper functions in a medical device. The "user" of a device refers to anyone who interacts with the device and includes without limitation a patient, a caregiver and a manufacturer of the device.

The information related to the patient or device may further include information related to regulatory approval of the medical device. When new devices or device functions are developed, they typically need to gain approval from one or more regulatory bodies such as the FDA. If the medical device is to be marketed worldwide, the new functions typically need to be approved by several regulatory bodies. These regulatory bodies often have jurisdictions over different geographic areas. The result is that an approval status for a medical device (or, of certain functions of a medical device) may vary with geographic area. These geographic jurisdictional areas may include multiple countries such as the European Union (EU). Also, one country may base its regulatory approval on a regulatory approval of a body from another geographic jurisdiction, such as when regulatory approval in a non-EU country follows the approval of the EU. Additionally, a regulatory body may give limited approval before full approval, such as approval for a research study or approval for clinical trials. Also, a regulatory body may allow use of a device, a function of a device, or both, for emergency use before the device or function receives full approval. Typically, device manufacturers deal with this problem by providing several models of a medical device with each model having a different set of unalterable functional capabilities, or by holding up distribution until the devices have gained approval. These approaches generate additional overhead costs from the operation of multiple manufacturing lines, management of additional inventory and marketing of a multiple device product line.

In one example, these problems are avoided by providing complete functionality in all model versions of a medical device and providing an updated set of active functions based on the new information related to the patient and/or device. This is accomplished by providing the ability for a medical device to dynamically configure a set of one or more active functions from a set of one or more performable functions when the device receives the information. These medical devices include a controller circuit such as a microprocessor or microcontroller. The controller circuit executes instruction code to perform the various functions. According to some embodiments, all functionality resides in the device and a section or sections of corresponding instruction code are enabled to allow the medical device to provide the particular function. Conversely, these areas of instruction code are disabled to inhibit the function. For example, the enabling and disabling can be realized by branching to or around the pertinent areas of instruction code. In some embodiments, the enabling and disabling includes applying or removing power to circuitry that provides the functions, such as therapy circuitry for example. In some embodiments, the medical device is given an identifier after the update to reflect the new functionality, such as a new model number or dash or revision number appended to or otherwise associated with the model number.

In other embodiments, new instruction code is loaded into the device to provide a new function or set of functions. In some of these embodiments, this instruction code can be loaded into volatile memory from a second device, such as when a need for the updated code is recognized by the medical device or the second device. In another embodiment, the medical device contains writeable non-volatile memory such as flash-memory, and the instruction code is loaded into the flash-memory. In this embodiment, the medical device includes a basic kernel of instruction code to load and begin executing the downloaded instruction code. In other embodiments, the controller circuit checks the downloaded code for errors before loading the updated code into flash memory. In one such embodiment, the updated instruction code is first loaded into volatile memory and checked for errors. In another embodiment, the instruction code is checked for errors as it is received from the second device. The medical device may also include a write circuit that provides the voltages necessary to write non-volatile memory.

The medical device receiving the updated instruction code can be either an external device (such as an external cardioverter defibrillator, for example) or an implantable medical device (IMD) (such as an implantable cardioverter defibrillator, for example). The second device sending the instruction code can be an external device such as a computer, an IMD programmer, or a repeater, or the second device can be an external medical device or another IMD. The term "repeater" refers to a device that rebroadcasts information it receives. For example, a repeater may receive information by wired or wireless telephone or a wired or wireless connection to a communications network, such as the internet, and may rebroadcast the information using wireless communications, or vice versa. In this way, a repeater placed in proximity to a patient can communicate with an IMD thereby providing a user with a method to remotely communicate with an IMD.

FIG. 1 illustrates an embodiment of a system 100 that uses an implantable medical device (IMD) 110. The system 100 shown is one embodiment of portions of a system used to treat a cardiac arrhythmia. A pulse generator (PG) or similar electronics unit or other IMD 110 is coupled by an intravascular or other cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also includes an IMD programmer or other external device 170 that typically provides wireless communication signals 160 to communicate with the IMD 110, such as inductive signals or radio frequency (RF) signals. In some embodiments, the IMD 110 is able to communicate wirelessly with another IMD 110.

Cardiac lead 108 includes a proximal end that is coupled to IMD 110 and a distal end that includes an electrode or electrodes. The distal end is coupled to, or placed in proximity to, one or more portions of a heart 105. The electrodes are for delivering atrial or ventricular cardioversion/defibrillation or pacing or resynchronization therapy to the heart 105. IME 110 includes components that are enclosed in a hermetically-sealed canister or "can." Additional electrodes may be located on the can, or on an insulating header, or on other portions of IMD 110, such as for providing unipolar pacing or defibrillation energy, for example, in conjunction with the electrodes disposed on or around heart 105. The lead 108 or leads and electrodes are also typically used for sensing intrinsic electrical activity of a heart 105 or for sensing impedance associated with a heart or thorax.

Figure 2:
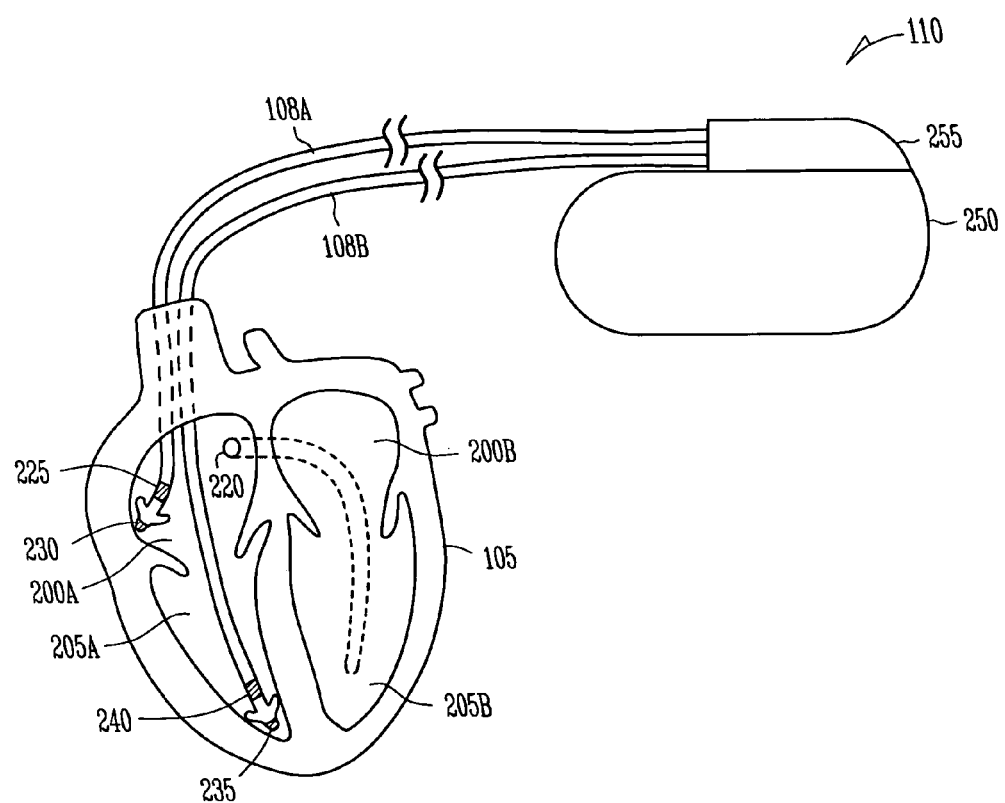
FIG. 2 is an illustration of an implantable medical device.

FIG. 2 illustrates an IMD 110 coupled by one or more leads 108A–B to heart 105. Heart 105 includes a right atrium 200A, a left atrium 200B, a right ventricle 205A, a left ventricle 205B, and a coronary sinus 220 extending from right atrium 200A. In this embodiment, atrial lead 108A includes electrodes (electrical contacts, such as ring electrode 225 and tip electrode 230) disposed in, around, or near an atrium 200A of heart 105 for sensing signals and/or delivering pacing therapy to the atrium 200A. Lead 108A optionally also includes additional electrodes, such as for delivering atrial and/or ventricular cardioversion/defibrillation and/or pacing or resynchronization therapy to heart 105.

Ventricular lead 108B includes one or more electrodes, such as tip electrode 235 and ring electrode 240, for delivering sensing signals and/or delivering pacing therapy. Lead 108B optionally also includes additional electrodes, such as for delivering atrial and/or ventricular cardioversion/ defibrillation and/or pacing therapy to heart 105. IMD 110 includes components that are enclosed in a hermetically-sealed canister or "can" 250. Additional electrodes may be located on the can 250, or on an insulating header 255, or on other portions of IMD 110, for providing unipolar pacing and/or defibrillation energy in conjunction with the electrodes disposed on or around heart 105. Other forms of electrodes include meshes and patches which may be applied to portions of heart 105 or which may be implanted in other areas of the body to help "steer" electrical currents produced by IMD 110. In one embodiment, one of atrial lead 108A or ventricular lead 108B is omitted, i.e., a "single chamber" device is provided, rather than the dual chamber device illustrated in FIG. 2. In another embodiment, additional leads are provided for coupling the IMD 110 to other heart chambers and/or other locations in the same heart chamber as one or more of leads 108A–B. The present methods and systems will work in a variety of configurations and with a variety of electrical contacts or "electrodes." The methods and systems also work in medical devices, implantable or external, that do not include leads or electrodes.

Figure 3:
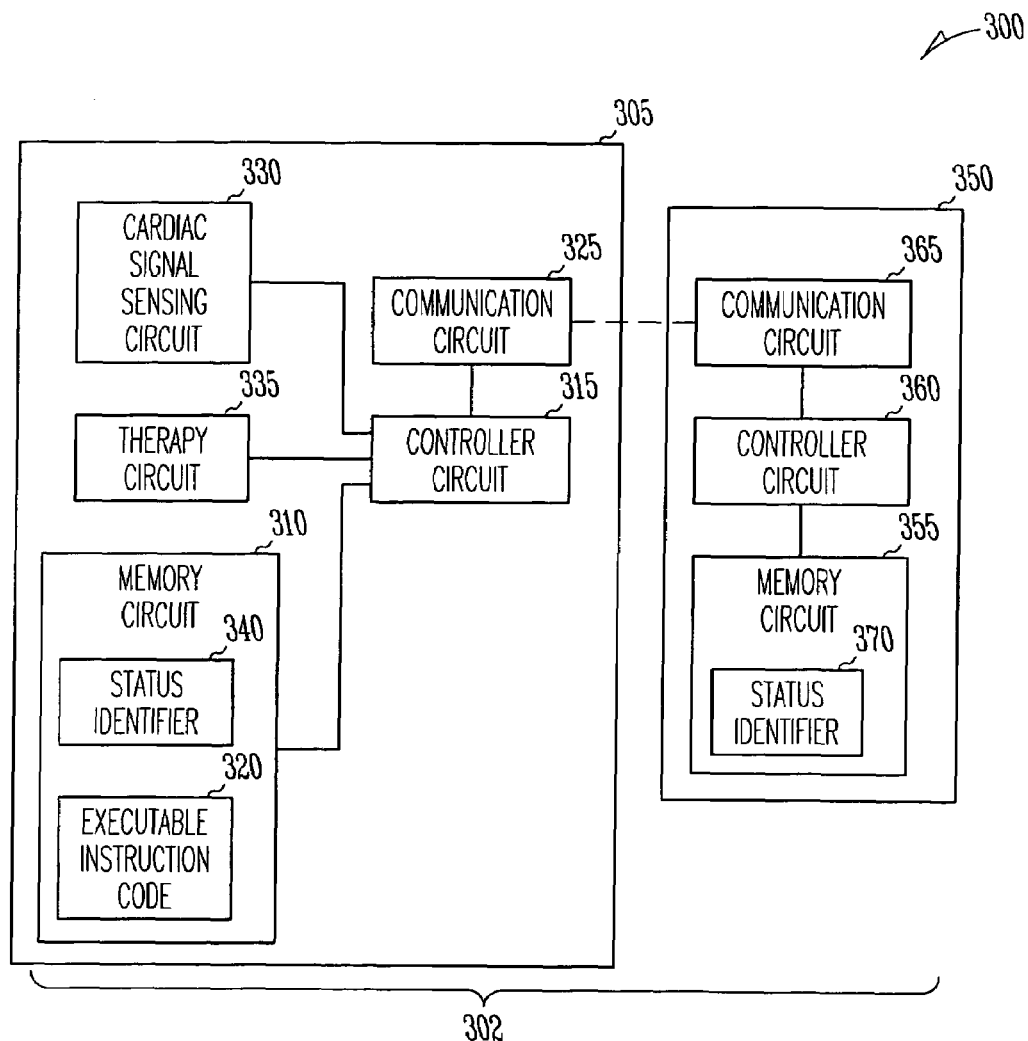
FIG. 3 is a block diagram of portions of an embodiment of a system that manages medical device functions.

FIG. 3 is a block diagram 300 of portions of an embodiment of a system 302 that manages medical device functions. The system 302 includes an IMD 305 and a second device 350. The IMD 305 includes at least one memory circuit 310, which is either separate from or integral to a controller circuit 315 coupled to the at least one memory circuit 310. The memory circuit 315 stores instruction code 320 executable by the controller circuit 315 to perform at least one function. The IMD 305 also includes a communication circuit 325 for communication with the second device 350. The second device 350 includes at least one memory circuit 355, which is either separate from or integral to a controller circuit 360 coupled to the at least one memory circuit 355, and a communication circuit 365. A controller circuit 315, 360 operates using hardware, firmware, software or any combination of hardware, firmware and software.

The IMD 305 is dynamically configured after information is received that is related to regulatory approval of a device function. The term function includes, among other things, any diagnostic test or measurement performed by a medical device (in this embodiment, an IMD 305), any sensing function, any therapy delivered or performed by a medical device, or a medical device communicating using an approved operating frequency. In the example of FIG. 3, the IMD 305 includes at least one cardiac signal sensing circuit 330 to detect cardiac signals, and the at least one function includes a diagnostic test. In another embodiment, the IMD 305 further includes a therapy circuit 335 coupled to the controller circuit 315, and the at least one function includes a therapy delivered to a patient.

At least one of the memory circuits 310, 355 of the IMD 305 and the second device 350 stores at least one status identifier 340, 370 corresponding to a regulatory approval status of the at least one function. The status identifier 340, 370 is used to enable or disable the at least one function. According to some embodiments of the system 302, at least the memory circuit 310 of the IMD 305 stores the status identifier 340. In some examples, the second device 350 is operable to communicate at least one approved function to the IMD 305, and wherein the IMD controller circuit 315 is operable to compare at least one performable function to the approved function and update at least one status identifier 340 in accordance with an outcome of a comparison. In an example, the second device 350 may communicate a set of one or more functions to the IMD 305 that the IMD 305 is to perform. The IMD controller circuit 315 compares a set of active functions to the set obtained from the second device 350 and updates the corresponding IMD status identifier or identifiers 340 to match the set of active functions obtained from the second device. In another example, the second device sends one approved function at a time. The IMD 305 updates the corresponding IMD status identifiers 340 as the approved functions are communicated. In this example, any non-communicated functions are deemed to be disabled.

In other embodiments, at least the memory circuit 355 of the second device 350 stores the status identifier 370. The second device 350 communicates the status identifier 370 values for storage into the IMD memory circuit 310 to enable or disable functions. According to yet other embodiments, the memory circuit 355 of the second device 350 stores the status identifier 370, and the second device 350 enables or disables the at least one function in the IMD 305 in accordance with the regulatory approval status. In another embodiment, the memory circuit 310 of the IMD 305 stores the status identifier 340, and the IMD 305 is operable to communicate an enabled or disabled status of the at least one function to the second device 350.

To enable or disable the function, in certain examples, the IMD controller circuit 315 reads a first value in the status identifier 340 that indicates that the corresponding function is not approved by the applicable regulatory authority. Upon reading the first value, the corresponding function is disabled and the controller circuit 315 does not perform that function. For example, reading the value may cause the controller circuit 315 to branch around the executable instruction code corresponding to that function. When the controller circuit 315 reads a second value in the status identifier 340 to indicate that the corresponding function is approved by the applicable regulatory, that function is enabled and the controller circuit 315 performs that function.

In other examples, the second device controller circuit 360 reads a first value or a second value in the status identifier 370 that indicates that the corresponding function is not approved or approved by the applicable regulatory authority. Upon reading the first or second value, the second device 350 communicates a disable or enable to the IMD 305 and the corresponding function is disabled or enabled by the IMD 305. In further embodiments, a model number or a dash number of the IMD 305 is changed, such as to reflect the corresponding updated functionality.

In other embodiments, the system 302 further includes a geographic location identifier stored in at least one of the memory circuits 310, 355 to identify the IMD 305 with a location. In one example, the location specifies where the device is deemed to be located (i.e. where the medical device is used or the patient resides). The location may alternatively specify where the device 305 was implanted. In one example, the value of a status identifier 340, 370 enables or disables the corresponding function or functions in accordance with a regulatory approval status for the geographic location specified by the corresponding stored geographic location identifier. In one example, the memory circuit 310, 355 includes a table or set of tables. The table includes locations where the function is approved. In another example, a set of tables includes geographic locations organized into tables by jurisdiction. Regulatory approval in a jurisdiction is reflected by an entire table of locations becoming approved. If the geographic identifier is found in a table of approved locations, and the status identifier value is set to enable a function, then the controller circuit enables that function. If the geographic identifier is not found in a table of approved locations, and the status identifier value is set to enable the function, then the controller circuit does not enable that function. As discussed previously, which controller circuit 315, 360 enables or disables the function depends on where the status identifier 340, 370 is stored.

In certain examples, at least one of the IMD 305 and the second device 350 further includes a clock circuit coupled to the controller circuit 315, 360. The controller circuit 315, 360 is operable to enable or disable a function in relation to a time or date associated with a regulatory approval status. In one example, the controller circuit 315, 360 updates a status identifier with a new value at least partially in response to a time or date read from the clock circuit. In another example, the controller circuit 315, 360 performs a logic function (such as an "and" function) of the status identifier with the clock circuit value to enable or disable the function. In this way, a medical device can be programmed, in anticipation of an approval date, to start using a function after the anticipated approval date.

In another example, controller circuit 315, 360 uses a timing or clock circuit to provide a slot of time when the function is enabled or disabled. In the embodiment, the controller circuit 315, 360 enables or disables a function on a start date or time and disables or enables the function after a timed duration. For example, the controller circuit 315, 360 may update the status identifier with a new value during a timed duration, returning the status identifier to its previous value after the timed duration expires. In this way, a device may temporarily enable a medical device, such as for use in a clinical study. In another embodiment, to use a medical device in a clinical study, the device is deemed a clinical study device (such as by using a particular model number or dash number, for example). In one such example, the status identifier 340, 370 includes a third value to indicate that the function is approved for a clinical study purpose, and the third value enables the corresponding function in the clinical study device.

In another example, the status identifier 340, 370 includes a value to indicate that the function has an approved status during a patient emergency, and that value enables the corresponding function. In yet another embodiment, the timing or clock circuit provides a time slot where a function is enabled or disabled during an emergency. In a further embodiment, the emergency approved status is combined with the geographical location identifier information to provide the emergency function-enabled status in those geographic locations where such emergency use has obtained regulatory approval.

In some examples, the at least one function includes an operating frequency for communication between the IMD 305 and the second device 350. In one such example, the second device 350 communicates that a communication frequency (or frequencies) between the IMD 305 and the second device 350 has approval (for example, in a particular geographic location) from the appropriate regulatory body (such as the Federal Communications Commission (FCC), for example, in the United States). The IMD 305 then begins communicating using the approved frequency or frequencies.

In some examples, the second device 350 is another IMD. In one such illustrative example, the first IMD 305 administers a drug and the second device 350 is a cardiac rhythm management device providing electrical therapy.

In other examples, the second device 350 is an external device. In the examples, the memory circuit 355 stores information about one or more functions performable by the IMD 305. Such information is stored along with one or more corresponding current status identifiers 370, geographical identifiers, or both. The current status identifiers 370 indicate a most currently known regulatory approval status of the corresponding function. In some examples, the memory circuit 355 also includes at least one table including "device type" identifiers corresponding to any one or combinations of the performable functions. The term device type identifiers refers to any information that identifies the functionality of a device and includes model numbers, dash numbers, and the like. A particular device type identifier is communicated to a target device such as IMD 305 to reflect the new functionality of the device.

In one example, the second device 350 also includes a user interface for users to interact with the second external device 350. In some examples, the memory circuit 355 of the external device stores regulatory approval information. This includes regulatory approval by geographic location, or regulatory approval by jurisdiction. This information is used to update status identifiers in the IMD 305, for example, in accordance with the geographic location or jurisdiction or to enable and disable functions according to the information. According to some examples, the information can be entered into the second device 350 using the user interface. In some examples, the second device 350 receives the information from a third device. In another example, the second device 350 receives the information from the IMD 305.

In some examples, the second device 350 communicates over a network. In one such example, the second device 350 is an IMD programmer. In another example, the second device 350 is a repeater that communicates with the IMD 305 and a third device which is remote from the external device. In one example, such communication is carried out over a communication network. The communication network may be a wireless network such as a cell phone network, a telephone land line network, a cable television network, or a wired or wireless connection with a computer network, such as the internet. Examples of the third device include a user's computer or computer network, a server, a hospital computer network, a device manufacturer's "Advanced Patient Management" system, or the like.

Figure 4:
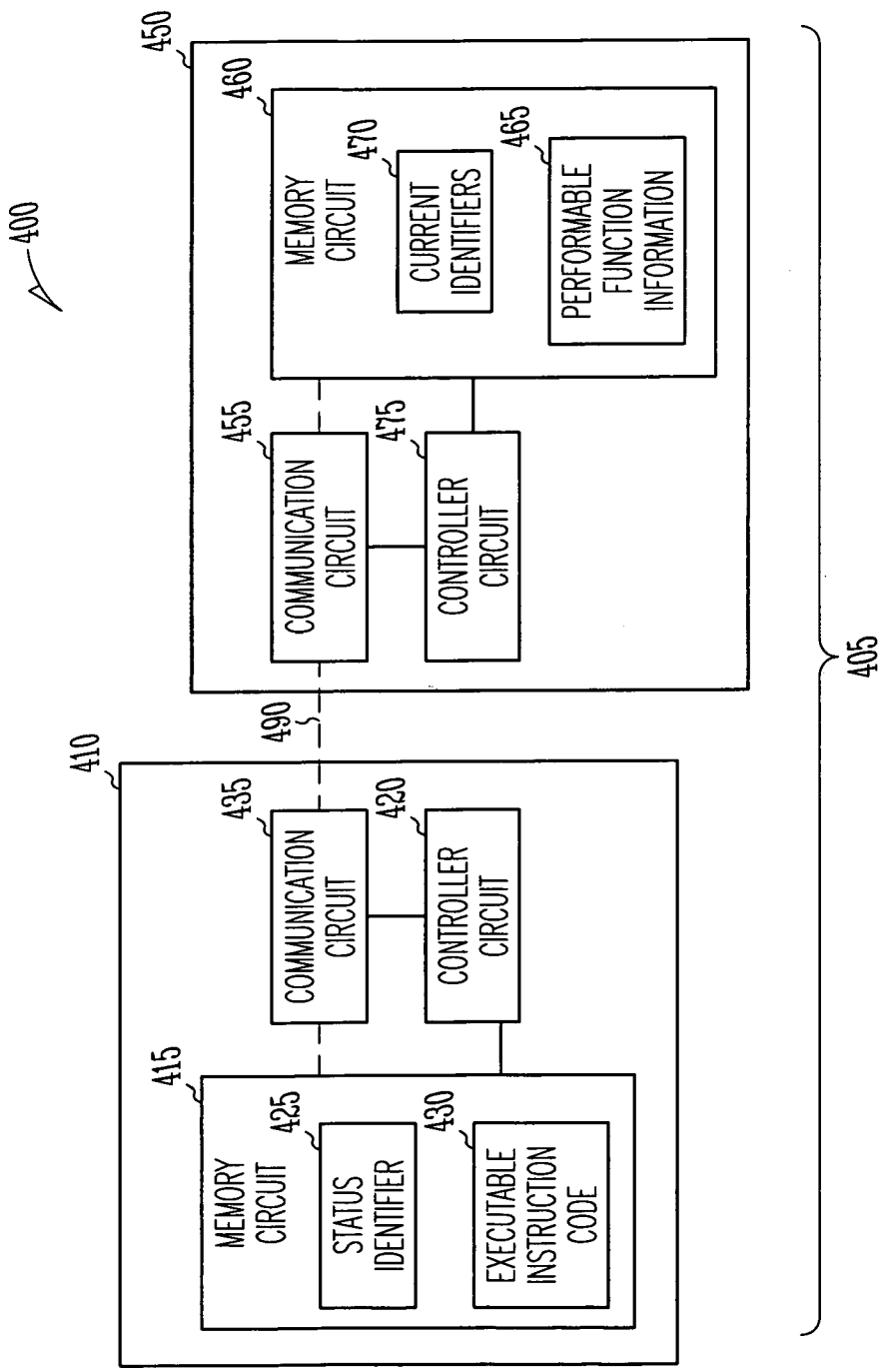
FIG. 4 is a block diagram of portions of an embodiment of a system that manages medical device functions.

FIG. 4 shows a block diagram 400 of portions of a system 405 that manages medical device functions. In this example, both the medical device and a second device are external devices. The system 400 includes a first external medical device 410 to perform diagnostic, therapeutic, or other functions. Examples of the first medical device 410 include, among other things, a blood glucose meter, an insulin pump, a urinalysis device, a fetal heart monitoring device, a blood test meter, a sleep apnea or hypopnea detection device, a sleep apnea therapy device, a blood pressure cuff, or a weight scale. The first external medical device 410 includes at least one memory circuit 415 and a controller circuit 420 coupled thereto. The memory circuit 415 stores instruction code 430 executable by the controller circuit 420 to perform at least one function. The memory circuit 415 also stores a corresponding status identifier 425 that enables or disables a corresponding function according to a regulatory approval status of that function. The first external device 410 also includes a communication circuit 435 coupled to the controller circuit 420.

The system 405 also includes a second external device 450 that communicates a regulatory approval status to the first device 410. The second device 450 includes a communication circuit 455 to communicate with the first device 410 and a memory circuit 460. The memory circuit 460 stores information 465 about one or more functions performable by the first device 410 along with one or more corresponding current status identifiers 470 of the most current regulatory approval status of a corresponding function. The second device 450 also includes a controller circuit 475 coupled to the communication circuit 455 and the memory circuit 460. The controller circuit 475 executes instructions to communicate the most current regulatory approval status to the first device 410 via the communication circuit 455. The devices 410 and 450 communicate via wireless or wired signals 490.

In some examples, the signals 490 are wireless communication signals, such as telemetry or radio frequency (RF) signals. In some examples, the at least one function includes communicating using a frequency of operation that is within a frequency spectrum approved by a regulatory body that regulates communication frequencies. In an illustrative example, the function includes communicating using frequencies within the Industrial Scientific and Medical band (ISM) or within the Short Range Devices (SRD) frequencies. In other examples, the signals 490 are communicated through a computer port such as a serial or parallel port. In further examples, the first and second devices 410 and 450 include web or other network interface circuits and the signals are communicated using the internet or other computer network.

In some examples, the controller circuits 420 or 475 execute instructions to retrieve and store information between the memory circuits 415 or 460 and the communication circuits 435 or 455. In other examples, the controller circuits 420 and 475 execute instructions to provide a starting address and block size information to the communication circuits 435 or 455, and the communication circuits 435 or 455 retrieve or store information from or to the memory circuits 415 or 460.

The system 405 operates similarly to the system discussed previously where the medical device is implantable. For example, the first medical device 410 performs similar functions of the IMD. In some examples, the first medical device 410 further includes a geographic location identifier stored in the memory circuit 415 to identify where the first device 410 is deemed to be located. A particular function's corresponding status identifier enables or disables that function in accordance with a geographic jurisdiction of a regulatory approval agency. In some examples of the first device 410, to enable or disable the function, the controller circuit 420 reads a first value in the status identifier 425 to indicate that the corresponding function is not approved. Upon reading the first value, that function is disabled and the controller circuit 420 does not perform that function. When the controller circuit 420 reads a second value in the status identifier 425 to indicate that the corresponding function is approved, that function is enabled and the controller circuit 420 performs that function. In another example, a third value of the status identifier 425 is used to designate that the function is approved for a clinical study purpose and the third value enables that function.

In some examples, the second device 450 communicates at least one approved function to the first device 410, and the controller circuit 420 of the first device 410 compares a set of performable functions to the approved function and updates any corresponding status identifiers 425 to enable or disable functions based on the comparison. In other examples, the second device 450 communicates one more status identifiers 425 or geographic identifiers associated with the regulatory approval status to the first device 410 for storage. In other examples, only the memory circuit 460 of the second device 450 stores the identifier or identifiers 470, and the second device 450 enables or disables the at least one function in the first device 410 in accordance with the regulatory approval status. In other examples, the memory circuit 415 of the first device 410 stores the at least one status identifier 425, and the first device 410 is operable to communicate an enabled or disabled status of the at least one function to the second device 450.

In some examples, at least one of the first and second devices communicates over a network with a third device or devices using either communication circuits 435 and 455 or additional or other communication circuits. In some examples, the network includes a wireless communication network. In further examples, the network includes the internet, or another wired computer network. In one example, the second device is a repeater in communication with a third device over the internet either through hard wire or a wireless local area network (LAN). In another example, the first medical device 410 communicates wirelessly with another medical device such as an IMD.

Figure 5:
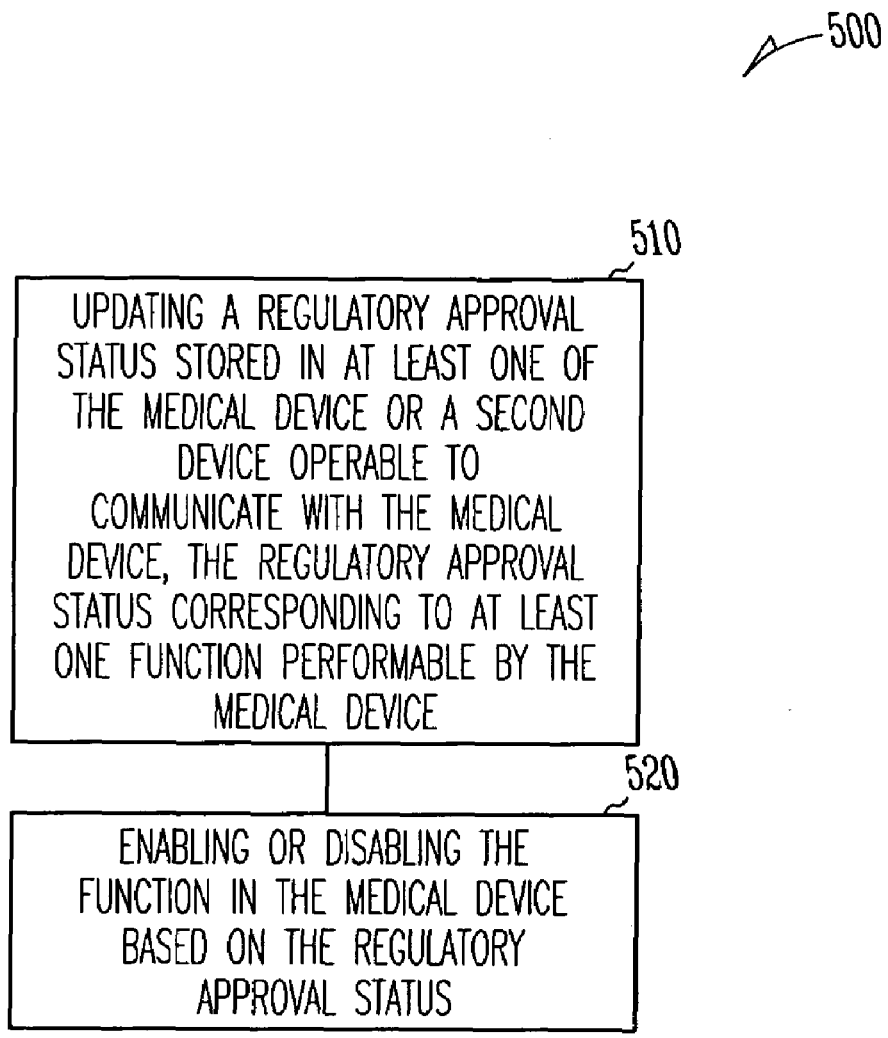
FIG. 5 is a block diagram of one example of a method of configuring a medical device.

FIG. 5 is a block diagram of one example of a method 500 of configuring a medical device. At 510, a regulatory approval status of at least one function performable by the medical device is updated. The status is stored in either the medical device, a second device operable to communicate with the medical device, or both devices. The medical device may be an external medical device or an implantable medical device (IMD). In one embodiment, the IMD is a cardiac rhythm management device. The second device may be an external device, an external medical device, or an IMD. At 520, the function is enabled or disabled in the medical device based on the regulatory approval status. The at least one function includes, among other things, one or more diagnostic functions, one or more sensing functions, one or more therapeutic functions, or communicating using approved communication frequencies.

In some examples, the method 500 further includes comparing a geographic jurisdiction of a regulatory approval body to a geographic location of the medical device, and updating the regulatory approval status of the function using the comparison. In some examples, the geographic location of the medical device includes a location where the medical device is deemed to be located. In one example, such location is deemed to be the home address of the patient or the location of a hospital or clinic frequented by the patient. In certain examples in which the medical device is an IMD, the geographic location is deemed to be a location where the medical device was implanted into the patient. In yet other examples, the location is an actual location of the medical device, such as determined by a global positioning system (GPS) or by communication with a particular node in a wireless or wired communication network that has a known geographic location.

In some examples, enabling or disabling the at least one function of the medical device includes setting a corresponding status identifier to a first value indicating that the function is not approved. This value is used to disable the device from performing that function. Enabling and disabling also includes setting the status identifier to a second value indicating that the function is approved. This value is used to enable the device to perform that function. The term "used to enable or disable" encompasses enabling and disabling in conjunction with other enables or disables to provide further logical functions of the device. For example, a status identifier may enable a function because it has regulatory approval and yet the function may remain disabled for another reason, such as because the function is not needed by the user. The values are used by either the medical device or the second device to enable or disable the function.

According to some examples, updating a regulatory approval status includes updating a regulatory approval status stored in the second device and communicating at least one identifier associated with the regulatory approval status to the medical device. The communicating may be accomplished using wireless communication signals or the communicating may be over wired connections. In the examples, enabling or disabling the at least one function in accordance with the regulatory approval status includes enabling or disabling the function using the medical device. In one example, a controller circuit of the medical device reads the value stored in its memory and branches around the executable instruction code corresponding to that function. When the controller circuit reads a second value in the status identifier to indicate that a corresponding function is approved by the applicable regulatory, that function is enabled and the controller circuit performs that function.

In another example, the enabling or disabling is done using the second device. The second device reads the identifier value stored in its memory and communicates with the medical device to enable or disable a function, or functions, performable by the medical device. In another example, the second device communicates at least one approved function to the medical device. The medical device compares at least one performable function to the approved function. The comparison may be done by using comparison circuitry, by executing instructions in a controller circuit in the medical device to perform a comparison, or both. Based on the comparison, the medical device then updates a regulatory approval status stored in the medical device.

In other examples, the regulatory approval is limited to using the device in a research study, or a clinical study. In some such limited approval cases, the enabling or disabling of the function in the medical device includes enabling the function when the medical device is deemed a clinical-use device. In some examples, such limited approval is accomplished by using a third value for a status identifier that enables the function when the medical device is identified as a clinical device, such as by communicating a clinical-use model or dash number to the device. In other examples, the function is enabled in relation to a date of the study, such as enabling using a date and/or time. The enabling can be done using the medical device or the second device. In other examples, the function is allotted a particular time window such that it is enabled only during the period of the clinical study. In one example, a function-enabled time window can be established using a timing or clock circuit in the medical device. The medical device updates a status identifier from one value to another during the time slot and returns the status identifier to the original value after the time slot. In another example, the timing or clock circuit is in the second device and the second device updates the status identifiers to enable or disable one or more functions.

In some examples, the regulatory approval is limited to use of the function only during a patient emergency (such as while the function awaits full regulatory approval). In these examples, the enabling and disabling of status identifiers includes enabling the function during a patient emergency. Either the first device or the second device may detect the emergency. In some of these examples, enabling the function during a patient emergency includes enabling the function for a timed duration and then disabling after the timed duration. As an illustrative example, suppose that the medical device is an implantable cardioverter defibrillator (ICD) and the function includes a particular defibrillation therapy. A regulatory body may allow use of the therapy only during predetermined patient emergencies.

In some examples, the method 500 further includes validating the at least one function having updated approval status. In some examples, the validating includes error-checking information that is associated with the function and stored in the medical device. The information includes parameters used to perform a function stored in the medical device. For example, the parameter may be a value corresponding to an output voltage. The information checked can also include instruction code executed to perform the function.

In some examples, the validating includes verifying that functions do not contain conflicting parameters. As an illustrative example, suppose that the medical device is a cardiac rhythm management device. In this illustrative example, a status identifier update may enable a function that requires electrical leads that are not present in the system. In some examples, the validating includes validating using the medical device, the second device or a combination of the first and second devices. If the function cannot be validated because of parameter or other conflicts, in one example, the second device is not allowed to interact with the medical device. This is useful, for example, where there is substantial interaction between parameters of multiple functions and it is not desirable to allow a user to have access to some but not all parameters.

In some examples, the method 500 further includes providing notification of an update of a set of active functions of the medical device. The notification is useful to a caregiver to be alerted to changes in capabilities of the medical devices. It is also useful to a manufacturer of devices to track the functionality of the devices. In some examples, providing notification includes providing notification of an update to a third device. For example, the third device may be a computer or server on a network such as the internet, a hospital local area network (LAN), an APM, or the like. The notification can be sent by wireless or other electronic communication methods. In some examples, the update is communicated to a database. The database includes stored updates of the set of functions of devices which may be in the field or in inventory. In some examples, the notification includes notice that a device with a certain serial number has an updated different type identifier based on an updated set of functions active in the device. Examples of such identifiers include model numbers or dash or revision numbers appended to or otherwise associated with a model number. Since either the first or second device can be an IMD or an external device, providing the notification can be carried out using an IMD or an external device.

Figure 6:
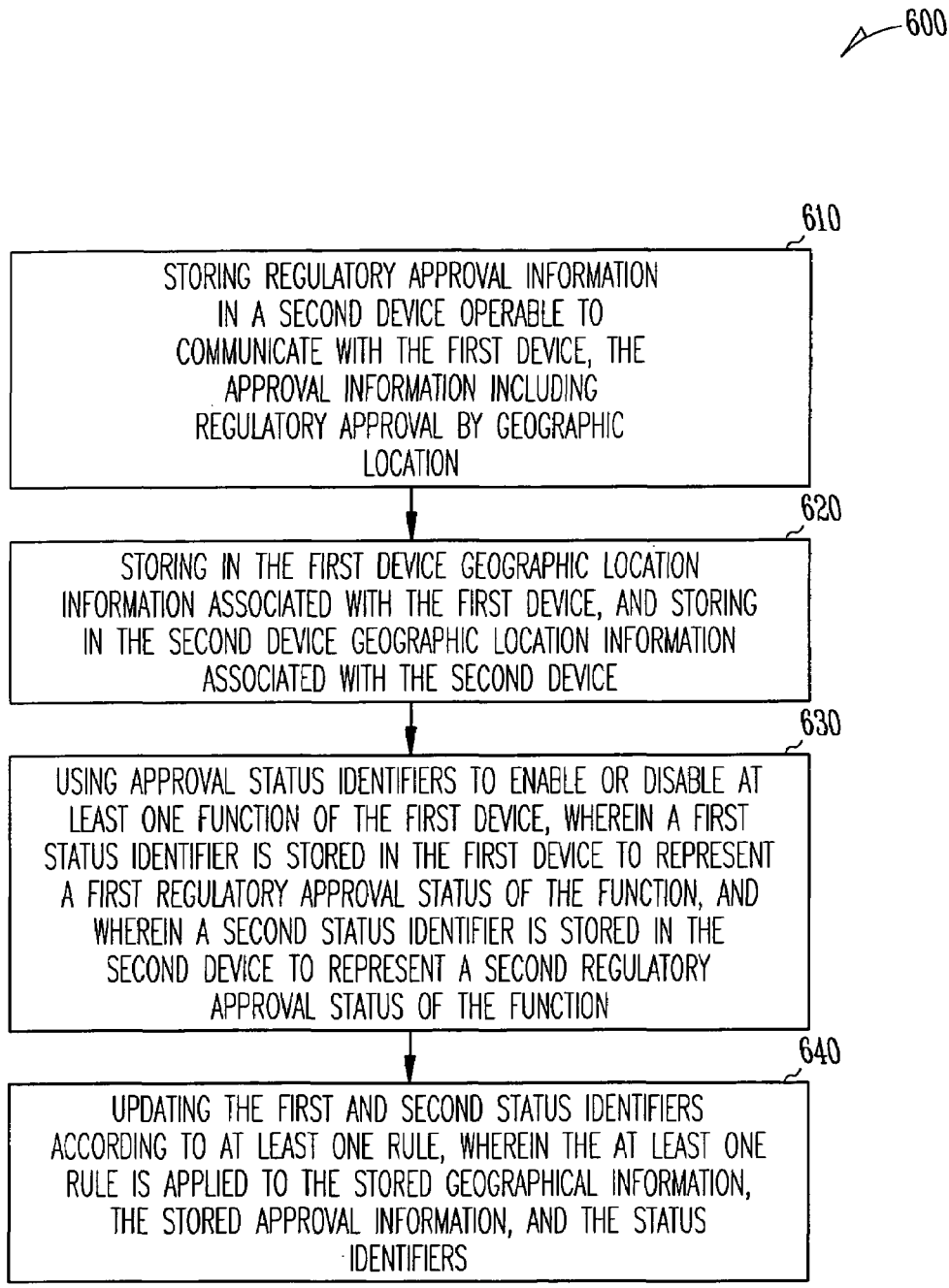
FIG. 6 is a block diagram of a method of activating or deactivating a function of a medical device.

According to some embodiments, the notification of the update is delayed. In some examples of the embodiments, a notification is sent by electronic mail (e-mail) and the notification is provided when the e-mail is opened. In other examples, the notification is delayed until the medical device is interrogated by either a user or another device. In other examples, the notification is provided through a user interface display on any of the mentioned devices, and notification is delayed until the next time a user interacts with the user interface Some of the embodiments discussed previously involve status identifiers stored in two devices. This raises an issue of how to handle the different circumstances that can arise when the identifiers agree, disagree, or when one, the other, or both of the identifiers are missing. FIG. 6 is a block diagram of a method 600 of activating or deactivating a function of a first medical device. At 610, regulatory approval information is stored in a second device that communicates with the first device. In one example, the regulatory approval information includes regulatory approval by geographic location. Approval by geographic location includes approval by country or region and corresponds to geographic jurisdictions of regulating bodies. At 620, geographic location information associated with the first device is stored in the first device and geographic location information associated with the second device is stored in the second device. The first medical device can be either an external medical device or an IMD. The second device can be an external device, an external medical device, or an IMD. In one example, the geographic location information associated with the first device includes a location where the device is deemed to be located. If the first device is an IMD, the geographic location information includes a location where the device is implanted, in one example.

At 630, one or more approval status identifiers are used to enable or disable at least one function of the first device. A first status identifier is stored in the first device to represent a first regulatory approval status of the function, and a second status identifier is stored in the second device to represent a second regulatory approval status of the function. In some examples, values are assigned to the status identifiers, such as a first value to indicate an approved status and a second value to indicate an unapproved status. Further examples include assigning a third value to indicate a limited approval, such as to one or more clinical trials.

At 640, the first and second status identifiers are updated according to at least one rule. In one example, the at least one rule is applied to the stored geographic information, the stored approval information, or the status identifiers. In some examples, updating the status identifiers in the first and second devices according to at least one rule includes deeming the function approved. In further examples, deeming the function approved includes indicating the availability of the function using the second device. For example, if the second device is an external device with a user interface, in one example, a display on the external device is used to indicate to the user that the function is available. In other examples, deeming the function approved includes deeming the function approved for clinical use.

In some examples, updating the first and second status identifiers according to the at least one rule includes deeming the function unapproved. In the example where the second device is an external device with a user interface, a display on the external device is used to indicate to the user that the function is unavailable, such as by either not displaying the option or "ghosting" the option on the display. In further examples, deeming the function unapproved includes preventing access to the first device using the second device, such as by not allowing the communications or by limiting the communications. In yet another example, deeming the function unapproved includes triggering an alarm or notification using the second device.

In some examples, updating the first and second status identifiers according to a rule or a set of rules includes updating to affect the most restrictive use of a function or functions subject to approval. For example, if applying a rule or set of rules to the information and identifiers results in one device allowing the function and a second device not allowing the function, use of the function is not allowed. In some examples, updating the first and second status identifiers according to a rule or a set of rules includes updating to affect the least restrictive use of a function or functions subject to approval. For example, if applying a rule or set of rules to the information and identifiers results in one device allowing the function and a second device not allowing the function, use of the function is allowed.

Table 1 below illustrates one example of a set of rules applied to stored geographical information, stored approval information, or status identifiers. The result of applying the rules is to allow or not allow use of one or more functions in a medical device. In the example shown, the first device is an IMD and the second device is an external device (PRM) to program the IMD. The PRM has a user interface including a display. The devices communicate using wireless signals. The embodiment is also applicable to two external devices or two IMDs. This example implements a set of rules that is more restrictive.

TABLE 1

| | | Function Rules | | |
| --- | --- | --- | --- | --- |
| Line No. | IMD/PRM Geography | PRM Function Status | IMD Function Status | Outcome |
| 1 | Same | Not approved | Not approved | Function not available. |
| 2 | Different | Not approved | Not approved | Function not available. IMD model available with geography window. |
| 3 | Same | Not approved | Clinical | Function available OR not available depending on geography. If available, then IMD model available with clinical window. |

TABLE 1-continued

| Line No. | IMD/PRM Geography | PRM Function Status | IMD Function Status | Outcome |
|---|---|---|---|---|
| 4 | Different | Not approved | Clinical | Function available OR not available depending on geography. If function available, then IMD model available with geography window. |
| 5 | Same | Not approved | Approved | Out of sync - raise alarm. Function not available. |
| 6 | Different | Not approved | Approved | Function available OR not available depending on geography. If function available, then IMD model available with geography window. |
| 7 | Same | Clinical | Not approved | Function not available (or available if IMD is deemed a clinical device). |
| 8 | Different | Clinical | Not approved | Function not available. IMD model available with geography window. |
| 9 | Same | Clinical | Clinical | Function available. |
| 10 | Different | Clinical | Clinical | Function available. IMD model available with geography window. |
| 11 | Same | Clinical | Approved | Out of sync - raise alarm. Function not available. |
| 12 | Different | Clinical | Approved | Function available OR not available depending on geography. If function available, then IMD model available with geography window. |
| 13 | Same | Approved | Not approved | Out of sync - raise alarm. Function not available. |
| 14 | Different | Approved | Not approved | Function not available. IMD model available with geography window. |
| 15 | Same | Approved | Clinical | Out of sync - raise alarm. Function not available. |
| 16 | Different | Approved | Clinical | Function available. IMD model available with geography window. |
| 17 | Same | Approved | Approved | Function available. |
| 18 | Different | Approved | Approved | Function available. IMD model available with geography window. |
| 19 | * | Missing | * | Function not available. |
| 20 | * | * | Missing | Function not available. |
| 21 | PRM Missing | * | * | Special geography window available. IMD model not available until geography is entered. |
| 22 | IMD Missing | * | * | IMD model not available. |

The first column of the table is merely the line number of the rules. The second column of the Table relates to the geographic location information. Both the IMD and PRM contain geographic information. The geographic location information can be the same for the two devices, different for the two devices, or the information may be missing from one or the other device. The third and fourth columns contain the status identifiers for the IMD and the PRM respectively. The status identifier can be approved, not approved, approved for clinical study, or missing. The fifth column contains the outcome of applying the rules to the geographic information and the status identifiers. THE IMD model number identifies the type of IMD. Changes in a set of active functions in the device are tracked by modifying the model number with a dash number.

Line 1 of the Table shows an example of the simple case of the IMD and PRM containing the same geographic location information and the status identifiers of both devices agree that the function is not allowed in the geographic location. The PRM is allowed to interact with the IMD but not use the function. Line 2 of the Table shows an example of the case where the geographical information is different, but the function is not allowed in either location. The PRM is allowed to interact with the device and the user interface includes a window notifying the user of the geographic difference.

Lines 3 and 4 of the Table show a case where the IMD is a clinical device but the PRM is not part of the clinical study. The function may be allowed if the geographic location of the devices approves use of the function outside of a clinical study setting. In this case, a clinical window is provided on the PRM user interface. If it is not approved, the function is not available. Because the geographic information of the devices differs, a geographic window is provided on the PRM user interface to notify the user of the geographic difference.

Lines 5 and 6 of the Table show examples of rules where the status identifiers conflict or are out of sync. Because the rules are more restrictive, in this example, the function is not allowed in line 5. In line 6 the function is allowed or not allowed depending on the geographical location. Lines 7 through 12 are examples of rules based on the PRM having a clinical status identifier for the function. Lines 13 through 18 are examples of rules where the PRM has an approved status of the function. Lines 13 and 15 show examples of rules where an alarm or other notification is raised because the status identifiers do not match.

Lines 19 through 22 are examples of rules applied when some information is missing. In lines 19 and 20, a status identifier is missing. In such cases, use of the function is not allowed, in one example. Another way to handle the case of missing identifiers is to not allow the PRM to interact with the IMD. This approach is useful if the function has substantial interaction with other functions and the missing information is important to know how to proceed. In line 21, the geographic location information for the PRM is missing. Interaction with the IMD is not allowed until information is entered in the PRM. A special window is displayed for the user to enter geographical information. In line 22, the geographic location information for the IMD is missing. In this case the PRM is not allowed to interact with the IMD. This case may arise when the IMD model is an old configuration or the PRM is not compatible with the IMD.

The Table is intended to show an example of a set of rules applied to stored geographical information, the stored approval information, and the status identifiers. Other examples can be utilized to implement other logical results. For example, other examples implement a set of least restrictive rules. Additionally, a more restrictive implementation may prevent more than just use of a function or set of functions. For example, most restrictive rules may prevent any interaction with the IMD in some circumstances. This is useful where there is substantial interaction between parameters of multiple functions and it is not desirable to allow a user to change some but not all parameters. Other examples of rules do not allow use of the function or functions if the geographic information does not match.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method of configuring a medical device, the method comprising:
    automatically comparing a geographical jurisdiction of a regulatory approval to a geographical location identifier stored in at least one of the medical device or a second device operable to communicate with the medical device;
    updating a regulatory approval status, stored in at least one of the medical device or the second device, in accordance with the comparison, the regulatory approval status corresponding to least one function performable by the medical device; and
    enabling or a disabling the at least one function in the medical device based on the regulatory approval status.

2. The method of claim 1, wherein a geographical location of the medical device includes a location where the medical device is deemed to be located.

3. The method of claim 1, wherein the medical device is an implantable medical device (IMD).

4. The method of claim 3, wherein a geographical location of the IMD includes a location where the IMD was implanted.

5. The method of claim 3, wherein the IMD is a cardiac rhythm management device.

6. The method of claim 1, wherein enabling or disabling the function includes setting a status identifier corresponding to the function to a first value indicating that the function is not approved, wherein the first value disables the function, or setting the status identifier to a second value indicating that the function is approved, wherein the second value enables the function, the status identifier stored in at least one of the medical device and the second device.

7. The method of claim 1, wherein updating a regulatory approval status includes:
    updating a regulatory approval status stored in the second device; and communicating at least one identifier associated with the regulatory approval status to the medical device;
    and wherein enabling or disabling the at least one function in accordance with the regulatory approval status includes enabling or disabling the function using the medical device.

8. The method of claim 1, wherein updating a regulatory approval status includes updating a regulatory approval status stored in the second device, and wherein enabling or disabling the at least one function in accordance with the regulatory approval status includes enabling or disabling the function using the second device.

9. The method of claim 1, wherein updating a regulatory approval status includes:
communicating at least one approved function to the medical device using the second device;
comparing at least one performable function to the approved function using the medical device; and
updating a regulatory approval status stored in the medical device in accordance with an outcome of a comparison.

10. The method of claim 1, wherein enabling or disabling the performable function based on the regulatory approval status includes enabling the function when the medical device is deemed a clinical-use device.

11. The method of claim 1, wherein enabling or disabling the performable function in the medical device based on the regulatory approval status includes enabling the function during a patient emergency.

12. The method of claim 11, enabling the function during a patient emergency includes wherein enabling the function for a timed duration.

13. The method of claim 1, wherein the at least one function includes performing a diagnostic test.

14. The method of claim 1, wherein the at least one function includes providing a therapy to a patient.

15. The method of claim 1, wherein the at least one function includes communicating using an approved communication frequency.

16. The method of claim 1, wherein the at least one function includes performing a sensing function.

17. The method of claim 1, wherein the method further includes validating the at least one function having updated approval status.

18. The method of claim 17, wherein the validating includes error-checking of information associated with the function and stored in the medical device.

19. The method of claim 17, wherein the validating includes verifying that functions do not contain conflicting parameters.

20. The method of claim 17, wherein the validating includes validating using the medical device.

21. The method of claim 17, wherein the validating includes validating using the second device.

22. The method of claim 1, wherein the method further includes providing notification of an update of a set of active functions of the medical device.

23. The method of claim 22, wherein providing notification of an update of a set of active functions of the medical device includes providing notification of an update to a third device.

24. The method of claim 22, wherein at least one device is an implantable medical device (IMD), and wherein providing notification of the update includes providing notification using the IMD.

25. The method of claim 22, wherein at least one device is an external device, and wherein providing notification of the update includes providing notification using the external device.

26. The method of claim 22, wherein providing notification of the update includes providing the notification over a conmmnication network.

27. The method of claim 26, wherein providing the notification over a communication network includes providing the notification to a central database.

28. A method of adjusting whether a function of a first medical device is active, the method comprising:
storing regulatory approval information in a second device operable to communicate with the first device, the approval information including regulatory approval by geographic location;
storing in the first device geographic location information associated with the first device, and storing in the second device geographic location information associated with the second device;
using approval status identifiers to enable or disable at least one function of the first device, wherein a first status identifier value is stored in the first device to represent a first regulatory approval status of the function, and wherein a second status identifier value is stored in the second device to represent a second regulatory approval status of the function; and
updating the first and second status identifiers according to at least one rule, wherein the at least one rule is applied to stored information including the stored geographical information and the status identifiers.

29. The method of claim 27, wherein using approval status identifiers includes assigning values to the status identifiers, wherein assigning a first value indicates an approved status and assigning a second value indicates an unapproved status.

30. The method of claim 28, wherein assigning values to the status identifiers includes assigning a third value to indicate an approval during clinical trials.

31. The method of claim 27, wherein updating the first and second status identifiers according to the at least one rule includes deeming the function approved.

32. The method of claim 31, wherein deeming the function approved includes indicating the availability of the function using the second device.

33. The method of claim 27, wherein updating the first and second status identifiers according to the at least one rule includes deeming the function unapproved.

34. The method of claim 32, wherein deeming the function unapproved includes preventing access to the first device using the second device.

35. The method of claim 33, wherein deeming the function unapproved includes triggering an alarm with the second device.

36. The method of claim 28, wherein updating the first and second status identifiers according to at least one rule includes deeming the function approved for clinical use.

37. The method of claim 28, wherein updating the first and second status identifiers according to at least one rule includes updating to effect the most restrictive use of the at least one function subject to approval.

38. The method of claim 28, wherein updating the first and second status identifiers according to at least one rule includes updating to effect the least restrictive use of the at least one function subject to approval.

39. The method of claim 28, wherein the first device is an implantable medical device (IMD).

40. The method of claim 39, wherein the second device is an IMD.

* * * * *

UNITED STATES PATENT AND TRADEMARK OFFICE
CERTIFICATE OF CORRECTION

PATENT NO. : 7,167,755 B2
APPLICATION NO. : 10/958628
DATED : January 23, 2007
INVENTOR(S) : Seeberger et al.

It is certified that error appears in the above-identified patent and that said Letters Patent is hereby corrected as shown below:

In column 18, line 36, in Claim 1, before "least" insert -- at --.

In column 19, line 24, in Claim 12, before "enabling" insert -- wherein --.

In column 19, line 25, in Claim 12, before "enabling" delete "wherein".

In column 19, line 66, in Claim 26, delete "conmmnication" and insert -- communication --, therefor.

In column 20, line 26, in Claim 29, delete "27," and insert -- 28, --. therefor.

In column 20, line 31, in Claim 30, delete "28," and insert -- 29, --, therefor.

In column 20, line 34, in Claim 31, delete "27," and insert -- 28, --, therefor.

In column 20, line 40, in Claim 33, delete "27," and insert -- 28, --, therefor.

In column 20, line 43, in Claim 34, delete "32," and insert -- 33, --, therefor.

Signed and Sealed this

Seventeenth Day of April, 2007

JON W. DUDAS
*Director of the United States Patent and Trademark Office*